United States Patent [19]

Boiarski

[11] Patent Number: 5,141,310
[45] Date of Patent: Aug. 25, 1992

[54] METHODS AND DEVICES FOR MEASURING THE SPECIFIC GRAVITY OF LIQUIDS

[75] Inventor: Anthony A. Boiarski, Columbus, Ohio

[73] Assignee: Miles Inc., Elkhart, Ind.

[21] Appl. No.: 676,552

[22] Filed: Mar. 18, 1991

[51] Int. Cl.⁵ .............................................. G01N 21/41
[52] U.S. Cl. .................................................... 356/133
[58] Field of Search ................. 356/128, 133, 135–137

[56] References Cited

U.S. PATENT DOCUMENTS

| | | | |
|---|---|---|---|
| 3,071,038 | 1/1963 | Vollmer | 356/133 |
| 3,778,165 | 12/1973 | Grubb et al. | 356/128 |
| 4,381,895 | 5/1983 | Hughes et al. | 356/134 |
| 4,834,104 | 5/1989 | Kreinick et al. | 128/633 |

FOREIGN PATENT DOCUMENTS

| | | | |
|---|---|---|---|
| 56-82434 | 7/1981 | Japan | 356/133 |
| 60-66137 | 4/1985 | Japan | 356/133 |
| 1280502 | 12/1986 | U.S.S.R. | 356/133 |

Primary Examiner—F. L. Evans
Attorney, Agent, or Firm—Roger N. Coe

[57] ABSTRACT

This invention relates to a device and a method for measuring the specific gravity of liquids, in particular, urine. This invention more particularly concerns a component of an automated system for urinalysis, either of humans or animals. The device may also be developed as a stand-alone unit and includes a dispenser, a sample container in which the liquid is dispensed and flushed, and a fiber optic sensor system to record the refractive index of the liquid. The invention is particularly suited for use with small clinical samples.

18 Claims, 13 Drawing Sheets

METHODS AND DEVICES FOR MEASURING THE SPECIFIC GRAVITY OF LIQUIDS

BACKGROUND OF THE INVENTION

1. Field of the Invention

This invention relates to a system for measuring the specific gravity of liquids, in particular, urine. This invention more particularly concerns an automated system for urinalysis, which includes a dispenser, a sample container in which the liquid is dispensed and flushed, and a fiber optic sensor system to record the refractive index of the liquid (a fiber optic refractometer).

2. Description of the Related Art

A. Specific Gravity

Specific gravity determinations serve a wide variety of purposes. This variable, obtained from various body fluids, particularly urine, is a part of almost all routine clinical diagnostic work-ups.

Specific gravity is a dimensionless term and relates, in the case of a solution, to the ratio of the weight (density) of a certain volume of the solution to that of an equal volume of a standard substance (e.g., water) at the same temperature. For solutions such as urine, specific gravity is related to the number, density, ionic charge and weight of the various species of dissolved solutes.

Specific gravity measurements are useful clinically because specific gravity alters as a function of abnormal states. For example, the specific gravity of urine varies as electrolyte disturbances occur. These disturbances accompany various diseases, for example, diabetes. Consequently, specific gravity values may be one indication of disease.

B. Clinical Analyses of Urine

Routine urinalysis, as practiced at the present time, involves three basic areas of investigation: a determination of the presence or absence of substances such as glucose, protein, occult blood, ketones, and so forth; a determination of specific gravity; and a microscopic examination of the urinary sediment. The first area of investigation usually involves the testing of the urine specimen with indicator papers or strips comprising reagent pads responsive to the urinary constituents to be determined. Indicator strips, usually in the form of single strips carrying multiple reagent pads responsive to the different urinary constituents to be determined, are dipped momentarily into the urine specimens, and the resulting color responses are compared to a color chart. Under present technology, separate analytical steps must be undertaken to determine urinary specific gravity and to microscopically examine the urinary sediment.

C. Specific Gravity of Urine

Urine is composed of various solutes in water (the solvent). Most of the solute in urine is non-liquid. The specific gravity of urine indicates the relative proportions of dissolved solid components to the total volume of the specimen tested, thus reflecting the relative degree of concentration or dilution of the specimen. Under appropriate and standardized conditions of fluid restriction or increased uptake, the specific gravity of a urine specimen measures the concentrating and diluting abilities of the kidney.

Because in urine, the solute consists of only dissolved solids, the refractive index (ratio of the phase velocity of light in a vacuum to that in a specified medium) of urine closely correlates with its specific gravity.

Normal human urinary specific gravity ranges from 1.003 to 1.035, but usually remains between 1.010 and 1.025. Specific gravities below 1.010 can be indicative of diabetes insipidus, a disease caused by the absence of, or impairment to, the normal functioning of the antidiuretic hormone. Low specific gravity may also occur in patients with glomerulonephritis, pyelonephritis, and various renal anomalies. Specific gravity is high in patients with diabetes mellitus, adrenal insufficiency, hepatic disease, and congestive cardiac failure. Therefore, urinary specific gravity determinations are useful in routine urinalysis as a screening procedure for detecting potentially abnormal clinical conditions. For veterinary applications, values of specific gravity extend up to about 1.08.

D. Methods of Measuring Urine Specific Gravity

Determination of urine specific gravity is of considerable clinical value in the understanding and clinical management of electrolyte disturbances. Therefore, complete urinalysis should, and usually does, include a specific gravity determination. This determination may be by direct or indirect methods.

Specific gravity may be measured directly or calculated from the measurement of a related property, e.g., osmolarity or ionic strength. Previous methods for determining specific gravity include use of hydrometers, urinometers, pycnometers, gravimeters, refractometers, and the like.

Three basic indirect measurements have been used to determine urine specific gravity:

a) the relative density measurable by a hydrometer which consists of a weighted float with a calibrated scale;

b) the refractive index, correlated in urine to the amount of dissolved solids, determinable by measuring the refractive index relative to water;

c) the osmolarity, wherein the dissolved solid content of urine is determined by measuring the temperature at which the sample freezes, based on the ability of solutes to lower the freezing point of water.

Other variations include a urinometer, a hydrometer adapted to measure the specific gravity of urine at room temperature. According to one method, a weighted float with a calibrated scale is immersed in at least 15 ml of urine. When the weight comes to rest, the meniscus of the urinometer is recorded. Adjustments must be made for room temperature, and for the presence of glucose or protein in the sample. The urinometer indicates the relative density of the sample which generally corresponds to the specific gravity of the sample.

The osmolarity/specific gravity of a sample can be determined by measuring the temperature at which the sample freezes. For example, a solution containing 1 osmol or 1000 mosm/kg water depresses the freezing point 1.86 degrees centigrade. Standard tables have been developed for comparing the measured freezing point to known osmolarities. From the determined osmolarity, the specific gravity can be estimated.

When only a small sample is available to test, the refractive index of the sample can be used to estimate the specific gravity. A refractometer is a laboratory instrument used to make this estimation. The refractometer measures the refractive index of the sample. The refractive index of the sample is related to the content of dissolved solids. Standard tables have been produced which correlate the refractive index of the sample with a known specific gravity.

There are also some instrumental applications which utilize the "falling drop" method in which the urine density is determined by the rate at which a drop of urine travels through an immiscible medium of known composition.

In the "falling drop" method, a drop of the sample is placed into an organic solvent, e.g., benzene, chloroform, and the speed at which the drop falls in the solvent is measured. Standard tables have been constructed which relate the speed of the sample drop through the solvent to the specific gravity of the sample. This method does not have a high degree of accuracy and is not suitable for large scale screening, or for very small amounts of sample, such as those routine in clinical practice.

Reagent strips made by Miles Labs (Ito, et al., 1983) correlate with refractometer readings on urine.

E. Problems in the Related Art

Most of the optical methods used to detect the refractive index of fluids, are based on exploiting the reflection and refraction phenomena which occur near the critical angle of light-liquid interface. They essentially consist of transmitting light through a transparent, light-conducting structure immersed in the fluid medium, so that light undergoes multiple internal reflections on the walls of the structure. The determination of the intensity of the light thus transmitted by multiple reflections, and the sudden variation of this intensity near the critical angle, thus permits the refractive index of the fluid to be determined. These instruments have many disadvantages. Many are fragile, yet bulky instruments, which require continuous cleaning, maintenance, and calibration to maintain their sensitivity and reliability. Some are hard to read because of meniscus must be viewed. In some urinometers, the sample adheres to the sides of the container holding the liquid sampler. Some, e.g., prisms for the transmission of light, are not accurate for turbid fluids.

Another problem for obtaining accurate readings is that the volume of urine obtained in the clinical sample may be inadequate for use of various measuring devices. Methods and devices are needed for analysis of small amounts of liquids, e.g., $< 1$ $\mu l$, preferably about 250 $\mu l$.

Most devices operate accurately only within a very narrow SG range and have problems for a wide range, for example, SG = 1.00 to a least 1.09.

F. Patents on Devices to Measure Specific Gravity

Harmer has reported several variations on an optical fiber refractometer. Pointing out that "Optical fibres are particularly useful in that they may be used in inaccessible places . . . " p. 106 (Harmer, A. L., "Optical Fibre Refractometer Using Attenuation of Cladding Modes," Battelle Research Institute, Geneva Switzerland in the Proceedings of the First International Conference on Optical Fiber Sensors, London, Institute of Electrical Engineering (April, 1983)), the author uses as an application example, the "measurement of charge-state in lead acid batteries by monitoring refractive index changes." This reference points out the importance of the angles of light striking the probe-liquid interface to achieve optimum sensitivity. Harmer expresses a belief that the novelty of his refractometer is that the probe-liquid interface could be varied and controlled by introducing alternating bends in a multimode fibre.

Sensitivity increases as the refractive index of the fibre approaches that of the liquid but generally with a corresponding decrease in efficiency. In U.S. Pat. No. 4,187,025, a device is described for producing a light signal corresponding to the refractive index of a fluid medium. In this device, a curved section of the device is immersed in the fluid to be measured. The purpose of this sensor is to detect changes in the state of a fluid with improved sensitivity. It appears most applicable to continuous monitoring of large amounts of fluid rather than to single measures of small amounts of fluid, such as those routinely collected clinically. Multiple curvatures are used to increase sensitivity.

U.S. Pat. No. 4,015,462 relates to a system in which a carrier matrix is incorporated with osmotically fragile microcapsules, with a colormetric determination of osmolarity when the capsules are in contact with a solution. This is an example of an indirect measure of specific gravity.

Another test means, device and method for determining the ionic strength or specific gravity of an aqueous sample, makes use of a polymer salt and an indicator means capable of producing a detectable response to ion exchange between the polymer salt and the test sample (U.S. Pat. No. 4,473,650; see also U.S. Pat. No. 4,376,827, U.S. Pat. No. 4,532,216).

U.S. Pat. No. 4,433,913 describes a device for determining the index of refraction of a fluid, especially that in lead-acid storage batteries, employing a fiber optic sensor.

In an approach to measuring the refractive indices of both a sample medium and a reference medium to improve sensitivity, two sensors are combined in a single measuring portable probe which is connected by a flexible cable to a housing unit which accommodates the source of light, photodetectors, a test data processor, and an indicator. An advantage of this device is that concurrent readings of both a sample and a reference medium may be made under the same environmental conditions.

The invention disclosed in U.S. Pat. No. 4,427,293 comprises a double optical probe to determine the refractive index of liquids. The advantage of the double probe is to measure concurrently the liquid to be tested and a reference liquid, so as to avoid artifacts in the readings due to environmental fluctuations which might affect sequential readings. The reference must be read under the same conditions in order to obtain a correct estimate of the refractive index of the tested liquid.

U.S. Pat. No. 4,240,747 discloses fiber optic sensors having complex, alternating curvatures to measure the refractive index of a fluid medium. The device also has an improved filtering system to reduce the risk of contamination from suspension cultures. Improved sensitivity of measurements made by this device is attributed to various geometries of curves of sections of the sensors immersed in the fluid to be measured.

Most of the devices invented by Harmer (cited as patents above) disclose different shapes of the devices for light path production and detection systems. These shapes reported are presented as improvements over the basic, earlier versions of refractometers which comprise an optical detector, a light source, and a light-conductive structure connecting the detector with the source.

U.S. Pat. No. 4,076,052 describes a method, composition and device for determining and physical readings that are functions of specific gravity.

U.S. Pat. No. 4,318,709 is directed to a means and a method for determining the ionic strength or specific gravity of a fluid sample.

U.S. Patent No. 4,376,827 describes the use of pH indicators to make a determination which is proportional to the ionic strength of a solution. The ionic strength is used to approximate specific gravity.

U.S. Pat. No. 4,318,709 uses test strips (?) for determining ionic strength or specific gravity of an aqueous test sample.

U.S. Pat. No. 4,639,594 presents a fiber optic probe for in situ sensing of liquid level, concentration and/or phase change which attempts to solve the problem of temperature standardization of the sample and the reference liquid, by pulling the reference liquid inside the probe.

U.S. Pat. No. 4,564,292 presents a refractometer representing an improvement over the prior art wherein the previously separated sample medium sensor and the reference medium sensor are merged into a single measuring probe.

G. Status of the Art

Because the determination of whether to treat a patient based on a urinalysis is often done on an outpatient basis, and because only small amounts of fluid may be present, quick and accurate results for small specimens are needed to institute treatment while the patient is present.

As reviewed in the previous sections, the specific gravity of a liquid is a measure of the density of the liquid with respect to water. Further, the refractive index of a liquid (an optical property) is also dependent on the density of the liquid. Therefore, a measure of the refractive index has been used to infer the density (i.e., specific gravity) of a liquid. A fiber optic sensing concept has been suggested for measuring specific gravity; however, complete systems have neither been suggested nor successfully developed for small volumes of liquid, in particular, as obtained for multiple tests in a clinical setting.

SUMMARY OF THE INVENTION

A general aspect of the present invention comprises an improved system for measuring the specific gravity of a liquid. The system is particularly useful for small clinical samples, especially those obtained for urinalysis of humans or animals. The system may embody a single, self-contained, portable unit; however, it is especially applicable in automated systems for complete urinalysis.

In its application to urinalysis, the invention makes use of a container, reservoir or well to hold a sample to be analyzed while a sensor is measuring the refractive index of the sample. A fiber optic sensor or probe for measuring the refractive index of the sample is positioned in the container so as to be totally immersed in the sample. It is important that the assembly of the container and the sensor or probe be such as to enable liquid in the container to be thoroughly and readily flushed from the container. In that regard, the container preferably has a wall or side surface which declines from the vertical in the direction that liquid normally discharges from the container. The opposite wall or side surface preferably is more vertically inclined. Thus, it has been found that a conically shaped container is very effective in the practice of the invention, especially when the axis of the cone declines from the vertical in the direction of liquid discharge. The apex of the cone is well suited to hold a small sample of liquid, but at the same time provide a depth of liquid sufficient to submerge a sensor.

The sensor is preferably a fiber optic type which has multiple curvatures in a sequence wherein successive curvatures are in opposite directions. Moreover, the radius of the curvature is preferably between about 2 and 4 times the cross-sectional diameter of the sensor itself. In an exemplary embodiment, the diameter of the sensor cross-section is 0.250 mm and the bend radius is 0.8 mm.

The refractive index of the material of the sensor should be greater than the refractive index of the liquid under study, but it should approach the refractive index of the liquid. Thus, for urinalysis the refractive index should be at least about 1.495 and preferably between about 1.40 and 1.50. The sensitivity of the sensor increases with the number of reverse curvatures and also with the ratio of fiber cross-sectional radius to bend radius.

Fiber optic sensors possessing refractive indices of the values described above are readily available from a number of sources. In some instances, these fibers are clad with a thin layer of a second material. Although cladding is optional, cladded fiber sensors have been found to be very effective in the practice of the invention. Cladding is likely to reduce attack on the integrity of the fiber-optical core by the liquid.

It has also been found that the sensor should be at an angle with respect to the horizontal in the container of the invention to promote cleansing of the sensor by a flushing liquid. Thus, the sensor preferably should be at an angle between about 30 to 60 degrees relative to the horizontal, more specifically, about 45 degrees. Conveniently, the sensor is positioned along the wall surface of the container over which liquid is discharged from the container.

The height or length of the wall surface of the container is also an important consideration. In general, the height should be sufficient to immerse the sensor and provide an adequate sample for analysis (a minimum of about 0.5 mm). In that regard, it has been found that a conically shaped outer portion of the container or well capable of retaining between about 30 and 50 µl of urine is an effective design, where the diameter is about 3 to 5 mm and the height is about 1 to 3 mm. The cone shape preferably defines an angle between about 30 and 60 degrees at the apex and its axis is preferably at an angle between about 30° and 60° from the vertical.

The fiber optic element is preferably omega-shaped, because this design has been found to be compact and sensitive, and also to transmit adequate signals for ready detection.

The sample container or well of the invention is preferably mounted in a larger container which serves as a drain cup. A pipette or other suitable dispensing device is provided to discharge liquid into the sample container. The measuring device is sized to deliver at least about 6 times the volume of sample held by the sample container, and preferably between about 6 and 8 times the volume of sample. Thus, when displacing water from a sample container of some 40 µl capacity, at least about 250 µl of urine should be added to flush the container and also provide a representative sample. When flushing urine from the container, a somewhat larger volume of water will normally be employed; viz. at least about 350 µl.

It was found that a well height of approximately 1 mm provides resistance to cavitation which tends to form bubbles in the well during pipetting.

When the dispensing device, preferably a pipette, is not supplying liquid to the sample container it may be movable to a park position within the drain cup if the sensor is part of a multipurpose device.

In the practice of the invention, assuming that the sample container is filled with water, sufficient sample or urine flows into the container to flush the water from the container and to fill the container with an adequate sample. An opto-electronic readout system consisting of an LED emitter, a solid-state photodetector and associated standard electronic hardware is used to remotely interrogate the sensor via fiber optic cables. By monitoring the amount of light transmitted through the fiber optic sensor circuit, the index of refraction is measured, which directly relates to liquid density in the container surrounding the fiber. Light, preferably from an LED within a control box, is passed through the fiber optic sensor in the container and thence to a light detector. The amount of light that leaks from the sensor into the sample depends on the refractive index of the sample. The remaining light is transmitted to the light detector; therefore, the loss in light between that input and that returning to the detector is a function of the refractive index of the liquid. Moreover, because the refractive index of the sample correlates with the density of the sample, the signal generated by the detector is also a function of the density and specific gravity of the sample.

Following the above observation of the sample, the dispensing device now moves to a position above the sample container and dispenses water into the container in a quantity sufficient to flush the urine sample from the container and replace it with a reliable water sample. Light is then passed through the fiber optic sensor, and the resulting signal generated by the detector provides a reference for comparison with the signal obtained previously from the sample. The specific gravity of the sample is thereby readily ascertainable.

The degree of sensitivity of the invention can be determined by the variation of the transmitted light intensity for a given variation of the refractive index of the fluid to be measured.

The light detector responds only to the light reaching the detector along the path and not the light which, because of the critical angle, passes into the liquid. The light intensity is converted by the detector into an output signal whose value represents the measured index of refraction. The measured index of refraction with such a probe is the true index of refraction and is a function of two parameters: 1) the light bending characteristics of the liquid; and 2) temperature.

Cladding may be employed around the fiber core to help control the refractive index of the material contacting the surface of the fiber.

The refractive index system of the invention has the following characteristics which present particular advantages for making measurements of small biological samples.

As explained above, only a small sample volume is required for the test. The volume generally used for a urine specimen for which multiple tests are to be performed, for example, is between 100–300 $\mu$l, preferably about 250 $\mu$l. This volume not only flushes the sample container but also provides an adequate sample.

A sequential measurement is taken of a reference liquid then under the same conditions. The reference standard is usually water, preferably distilled water.

Only a small volume of water is needed to flush out the sample container. The flush volume generally used for a urine sample is between 300–500 $\mu$l, preferably 350 $\mu$l.

The accuracy of the invention has been found to be excellent, within $\pm 0.001$ specific gravity units (this is equivalent to $\pm 0.0004$ index units). Carryover effects due to inadequate flushing of the container show only an error of the order $\pm 0.001$ specific gravity units or less.

A broad range of SG 1.00 to at least about 1.09, with a maximum SG of about 2, is covered by the specific gravity sensor.

The sensor is relatively insensitive to sample clarity or color, which is of great benefit given the well-known variability of clarity and color in urine, one of the biological materials to which this invention is directed. Measurements may be made on a highly turbid sample ranging from a clear to a colored suspension, with an error of $\pm 0.001$ specific gravity units or less.

Only a short time is required for taking the measurements, of the order of 1–2 seconds. This advantage means that answers may be provided quickly, and that many samples may be processed in a short period of time. These advantages are of particular importance in clinical settings and provide good cost-benefit ratios.

There are only minimal temperature effects on the system. The temperature range within which the system is operable, is about 10°–35° C. A preferred temperature for the test is about 23° C.

The cost of the system is very modest. No disposable materials are required, a factor which helps to reduce costs. The sensor element is easy to fabricate, and there are minimum effects due to sensor fouling. Protein buildups do not appear to be a factor.

BRIEF DESCRIPTION OF THE DRAWINGS

Other objects and advantages of the present invention will become apparent upon reading the following detailed description and upon reference to the drawings in which.

Figure 1:
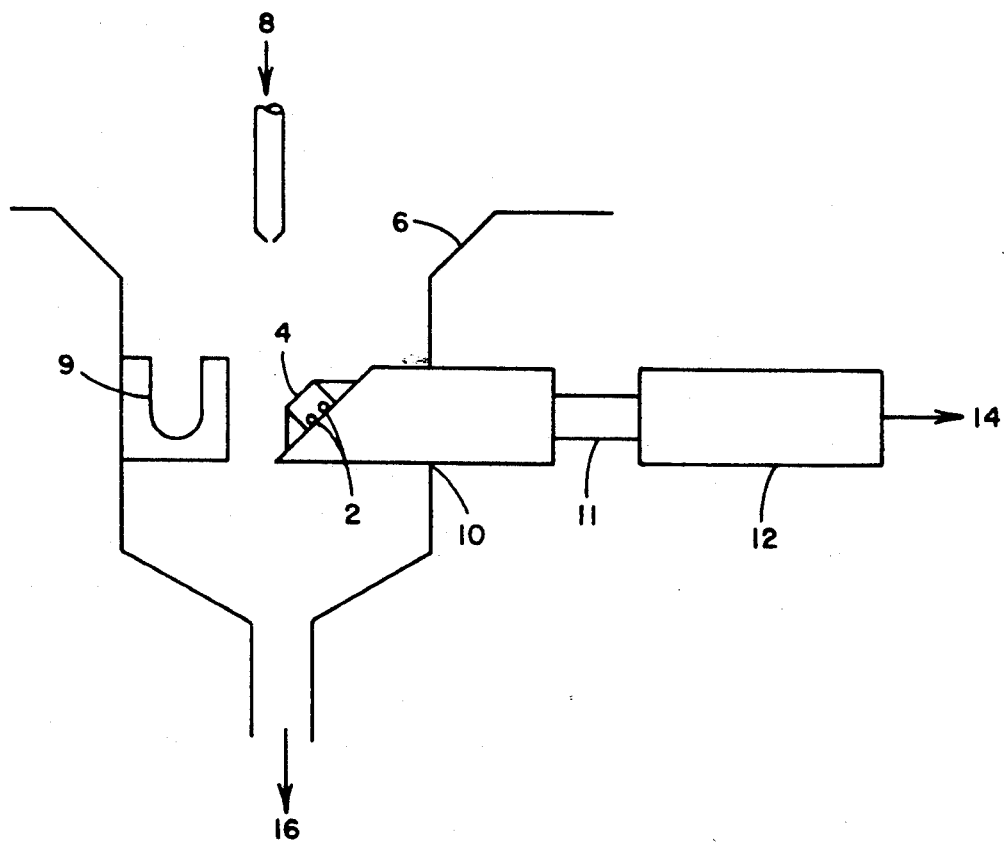
FIG. 1 is a block diagram of a breadboard specific gravity sensor system, indicating diagrammatically its relation to a larger system for complete automated urinalysis, e.g., the ATLAS presently under development to be manufactured by Miles Diagnostic Division.

While the invention is susceptible to various modifications and alternative forms, a specific embodiment thereof has been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DESCRIPTION OF THE PREFERRED EMBODIMENTS

1. Structure of the Device

Figure 2:
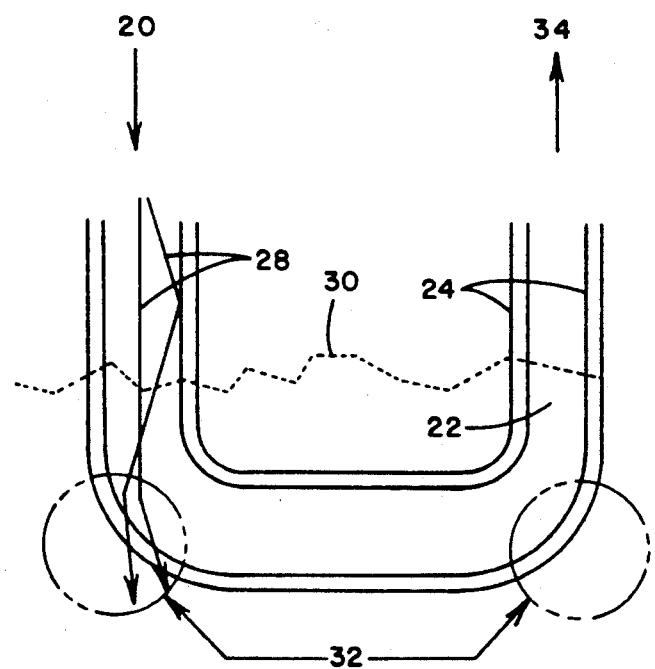
FIG. 2 is a diagram of the flow of refracted light from its source to a detector, through a U-bend sensing element in the liquid whose specific gravity is to be measured.

A basic device for measuring the specific gravity of a liquid is shown in the block diagram provided in FIG. 1. A sensor 2 and sample container 4, here shown in the form of a well, are located in the instrument drain port 6. A pipette 8 is positioned over the small container 4 to pipette fluid into the container 4. The pipette tip may be maintained in a wet park 9 if part of a multipurpose test device when not in use or when cleaning is performed. Submerged in the container 4 is the sensor 2 through which light is circulated. The sensor 2 is a small fiber optic device with multiple bends. FIG. 2 illustrates one shape of a sensor used for measuring liquid levels in various chemical processes using refractive index differences (GEM ® sensors, Division of IMO Delaval Inc.). A preferable number of reverse bends, given the size constraints of the liquid specimen used in this invention, is three to four (see FIG. 3 for a preferred embodiment). The sensor 2 is supported by a sensor holder 10, and is connected by fiber optics 11 to an emitter-detector module 12 which transmits information on light return to obtain transmission ratios. This information is used to calculate the refractive index of liquids in the container by a control box that may be part of a multi-purpose automated system 14.

Specifically, the pipette 8 introduces a small amount of a liquid sample (urine) into the container 4 to flush out previous liquid (water) and to provide a next sample for refractive index measurements. The pipette 8 operates on a flushing-measuring cycle, wherein water enters the container 4 from the pipette 8 after obtaining the urine specific gravity data to prepare for the next sample and also to obtain water reference data.

The container 4, shown in the form of a well, typically holds a small amount (≈30–50 μl) of sample for urinalysis during refractive index measurements on urine and water.

The sensor 2 measures the refractive index of the sample in the container 4 with good accuracy, over a broad specific gravity range and with minimal effects of variations in sample clarity.

Light travels along a cylindrical waveguide (i.e., optical fiber sensor 2). When water is present (SG=1.0), light negotiates the bends in the waveguide and returns to the emitter-detector module 12 which is connected to a control box 14 comprising a detector and data conversion control box. As the index of refraction (density) of the surrounding media increases, more light is lost, and the output signal decreases.

The opto-electronic module 12 obtains sample (e.g., urine and water) data from which a control box 14 accurately calculates specific gravity of urine based on water reference results.

The drain port 6 carries away excess sample and flush liquid from the sample container 4. The liquid drainage escapes into a drain bottle 16 or other suitable waste outlet.

2. Method of Operation

For urinalysis, using a multi-test automated system, reagent pad inoculations for other tests are carried out usually prior to specific gravity determination. The pipette 8 is then positioned over the container 4. Water initially in the sample well 4 is flushed out by a 250 μl volume of urine leaving 30–50 μl of urine in the well. Seconds later, after measurements on the urine have been made, about 350 μl of water are flushed through the pipette tip 8 into the container 4. This water flush clears out the urine in the container 4 and also cleans the inside surfaces of the pipette 8.

Following the water flush, the refractive index of the water is measured by the sensor 2. This water measurement is used to correct for any sensor drift that may have occurred since the last specific gravity measurement cycle. By always referring the urine specific gravity result to the water specific gravity (i.e., 1.0 value), specific gravity (SG) measurement accuracy is embellished.

After a water flush, the pipette 8 may be moved to the wet park station 9 where the outside portion of the pipette tip is cleaned by further water flushing and readied for a new cycle if part of a multipurpose test device. Alternative methods of cleaning and storing the tip are within the scope of this invention.

3. Specific Components of the Device

A. Sample Container

A preferred urinalysis container 4 comprises a well (specific dimensions 4.5 mm base diameter×2 mm long) which holds a specific, small amount of urine (approximately 40 μl) and can be easily flushed with water (small amount) so minimum carryover (previous sample contamination) occurs. The well 4 has a preferred outer surface shape of a cone with volcano-like edges plus specific dimensions mentioned above to provide 30–50 μl, preferably 40 μl, of sample volume. The sensor 2 is preferably at an angle (30°–60°) to the horizontal plane to facilitate flushing with a pipette 8. In an illustrative embodiment, the angle=45°. The pipette 8 is located in close proximity and slightly to the upstream end of the container to provide the best flushing (minimum carry over) conditions.

B. Sensor Size and Well Volume

Another important factor in the sensor design is the sensor size. This size factor is important because the sensor 2 must fit into the bottom of a container 4, and the container dimensions must be small to be compatible with usual sizes of urine samples and allowable for this portion of a multiple test analysis—i.e., about 100-300 μl. Other factors deemed desirable or important in the design of a preferred sensor and a sample well for urinalysis are as follows.

| | |
|---|---|
| Flush volume (water): | 300-500 μl |
| SG range: | 1.00-1.087 |
| Index range: | 1.333-1.370 |
| Accuracy: | ±0.001 SG units (±0.0004 index units) |
| Measurement time: | 1-2 seconds |
| Temperature range: | 10-35° C. |
| Carryover effects: | Error less than ±0.001 SG units |
| Sample clarity: | Clear to colored and highly turbid without error exceeding ±0.001 in SG |
| Protein buildup: | Minimize this effect |

In a design embodiment employing an omega-shaped sensor, selection of the sensor size involved picking a fiber diameter, d, which gave a small well diameter of approximately 18 d. This well diameter (18 d) was calculated by taking a sensor inside diameter of 6 d (R=3 d from results of the ray-trace model used to compare the output from an omega sensor to other models) and adding 2 d for the sensor fiber diameter and 10 d for clearance at the bottom of the container (5 d on each side). The container height was then chosen based on surface tension effects on the liquid in the container and overall container volume, $V_W$, which can be written:

$$V_W = 255\, d^2 h (\mu l) \tag{1}$$

where h is the container height. For a fiber diameter of 0.25 mm and a height h=2.25 mm, the container volume can be calculated to be 36 μl which is consistent with 250 μl urine sample and 350 μl water flush volumes, as discussed elsewhere in this specification.

The need for a small sensor size (i.e., small fiber diameter) must also be balanced by the need for a large input signal $I_S$ to the light detector. Therefore, d (see Eq. 3 hereinafter) must be large enough to provide adequate signal power. In the actual design referred to earlier, minimum $I_S$ was chosen to be 2 μW. Based on this choice, a 1 mw LED intensity was required in the actual design for $\epsilon_1 = 0.1$ and d=0.25 mm. Such an LED is available from several suppliers (e.g., Motorola, Honeywell, Hewlett Packard). The LED wavelength in the actual design was 820 nm, but other wavelengths could be used (e.g., 660 nm).

In summary, the sensor and associated well design used in urinalysis are driven by the need for:
1) Adequate sensitivity (approximately 40 percent change from a SG=1.0 to SG=1.05);
2) Good sensor transmission ($\approx 10$ percent) and adequate detector signal ($I_S \approx 2$ μW); and
3) Small sensor size (i.e., small fiber diameter) to match the small container volume size ($\approx 30$-50 μl) to minimize carryover effects.

The specific design referred to above provided for these factors.

C. Sensor System Design for Urinalysis

Sensor and liquid container designs are correlated because the following major parameters must be addressed in joint fashion namely:
1) sensor geometry;
2) well geometry; and
3) sensor and well size.

These parameters affect, and are affected by several other parameters, namely:
1) sensing fiber size;
2) minimum detector signal intensity; and
3) input LED (light emitting diode) intensity.

A specific design for urinalysis is required to provide required accuracy for small sample sizes—less than 1 ml and typically about 40 μl. Considering the constraints of the small specimen amount, and the desired sensitivity and accuracy, a computer program TRACE (obtainable from Battelle) was used to help generate configurations for a suitable sensor.

Curved shapes were preferred for a waveguide (sensor), and the number of bends in an optic fiber were correlated with light loss. The more bends in the sensor, the more sensitivity it has. There is a trade-off, however, in that increased sensitivity effected by increased bends, produces lower efficiency. For the purposes of this invention, keeping the specimen volume and container size relatively small (<1 ml), three to four bends are preferred.

U-bends, such as the example shown in FIG. 2, are marginally adequate but are not preferred. The sensor shown in FIG. 2 is one made of glass and manufactured by GEM ®, Inc. Light rays 28 enter the sensor from a source 20 and circulate through a glass element consisting of a core 22 with cladding 24. Some of the light rays 28 refract out of the sensor into the liquid 30 at the bends. The two regions of bends 32 form the "U" and determine the reading of the refractive index by determining the amount of light which returns to the detector 34.

Figure 3:
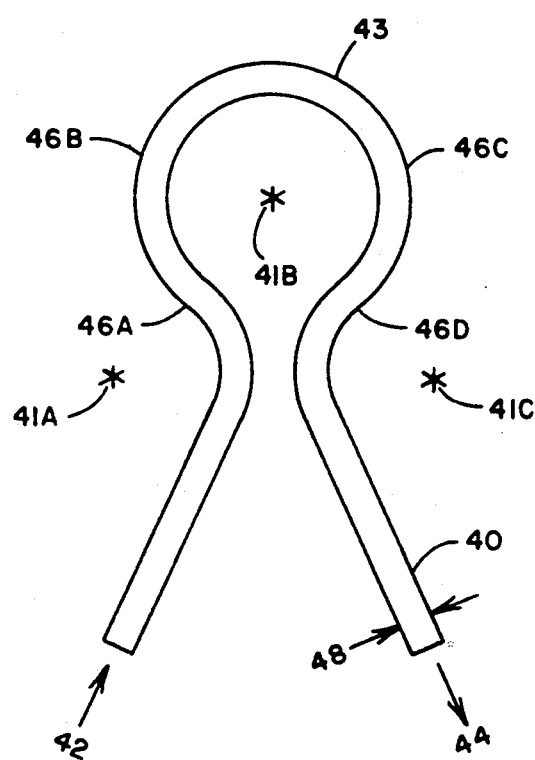
FIG. 3 is a diagram showing the geometry of a preferred sensor (i.e., an omega-shaped sensor) for the refractive index of a liquid.
Figure 4:
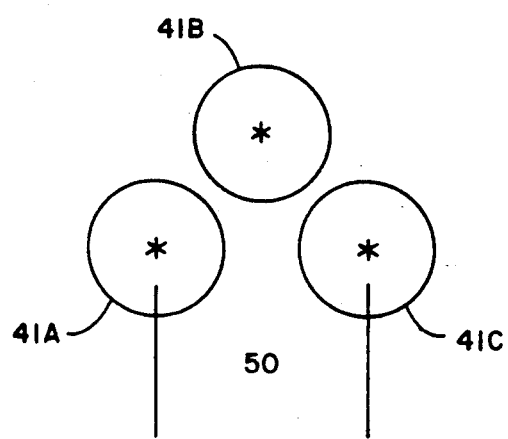
FIG. 4 is a drawing of a jig used to fabricate the sensor shown in FIG. 3.

The preferred shape having about three bends is that of an omega (FIG. 3). Light from a source 42 circulates through the fiber 40 and emits light 44 to a control box and detector 14. To make this shape, a polymer fiber 40 (ESKA produced by Mitsubishi) was heated to about 90° C. and placed on a jig (FIG. 4). The three stars 41A, B and C in FIG. 3 indicate the placement of three pins around which the heated fiber was formed These correspond to the position of the pins 41A, B and C in FIG. 4. These pins are generally 1/16" in diameter.

The jig is placed on a hot plate set at about 100° C. After the formation of the desired shape, the jig is cooled in a 25° C. water bath until the shaped fiber is set and can be removed. The fiber diameter is designated as 48 and preferably ranges from about 18 d where d is the diameter of the container 4 in FIG. 1.

A preferable sensor diameter for the specimen sizes used in urinalysis in accordance with this invention was 0.25 mm. Plastic acrylic) fibers are also preferred because they may be used to measure a broader range of refractive indices than glass. The index of refraction (n) of air=1, and that of $H_2O = 1.33$. That of urine can be as high as about 1.37. The sensors of the invention should therefore have an index greater than about 1.37. As explained more fully elsewhere in this application, the sensors preferably should be between 1.40-1.50.

The ESKA optical fiber mentioned above had a core index of 1.492 and a cladding 43 which surrounded the core. Cladding is not an essential component, but is present on commercially available fibers of this type and serves to protect the fiber core from liquids in which it is submerged. The thickness of the cladding should be small.

Although a more complex multicoiled sensor configuration is within the scope of this invention, such a sensor will tend to have constraints arising from the desired container and specimen size. At the other extreme, from a multiple bend sensor, a pencil shaped (i.e., single bend) sensor may be used to circulate light; however, this will generally be at a sacrifice of sensitivity. A pencil shaped sensor may be preferable for stand-alone, single purpose devices, e.g., portable devices with a built in control box.

Figure 5A:
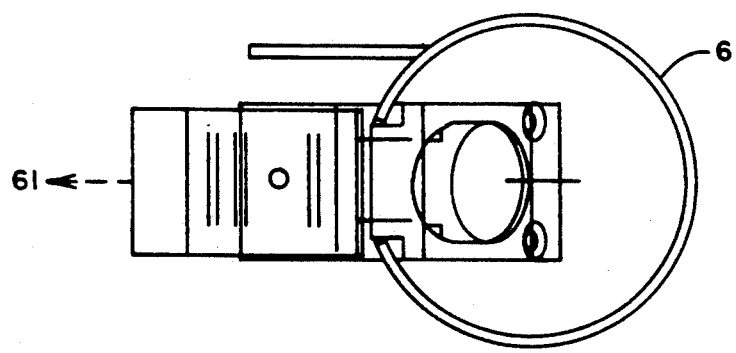
FIG. 5 is a diagram drawn to scale of an omega sensor based refractometer system; A) is a plan view of the drain cup rim surrounding the container and optional connectors to the optical electrical system; B) is a plan view showing the omega sensor position within the container; and C) is a cross-sectional view of the entire system.

FIG. 5A, B and C show a planar view of a preferred embodiment of the invention. FIG. 5A shows the rim of the drain cup (drain port) 6 surrounding the container 4 which is housed in the sensor holder 10 (see FIG. 1) and fiber optic leads from the optical electric module 12 through an optional connector to the main control box 61.

Figure 5B:
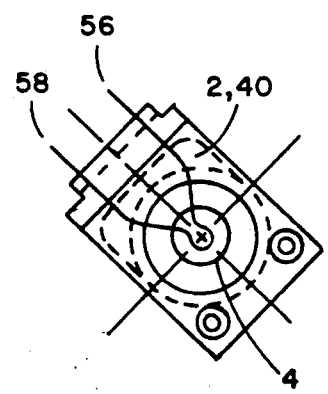

FIG. 5B is a planar view of the omega sensor 2 (FIG. 1), 40 (FIG. 3) placed in the bottom of the container 4. The light circulates through the input-output fiber wings 56, 58 which connect to the light source and the detector (not shown). In an illustrative embodiment, a 500 μm plastic fiber (ESKA No. 20) is used in the interconnect cable to the LED and 250 μm plastic fiber (ESKA No. 10) for the sensor itself. This 2-to-1 diameter difference minimizes misalignment effects at the bulkhead connector and also maximizes light throughout. In a preferred embodiment, a single fiber optic is used to eliminate light loss at the 500 μm-200 μm interface. A connector is not required. The bulkhead connector may be eliminated and a single long 250 μm fiber may be used with connectors on each end and the omega sensor in the middle.

The wavelength of the light source (LED) should normally range from about 660 nm to 1300 nm. It will be noted, however, that the upper end of this range is not generally suitable for plastic optical fibers. A (LED) wavelength of about 820 nm, a near infrared light, is preferred for plastic sensors. A wavelength of 660 nm has an advantage of better transmission, but the fiber core material will have a slightly higher index at 660 than 820. Laser sources with wavelengths of about 850 microns or less may also be employed. In general, changes of wavelength in the effective range, tend to effect sensitivity and efficiency.

Light sources useful in the present invention are standard equipment and are available commercially, e.g., Motorola, Honeywell, Hewlett Packard. Using a 1 mw source, 250–300 μm of light circulates through the sensor. 5–10% of the light generally returns to the detector.

Figure 5C:
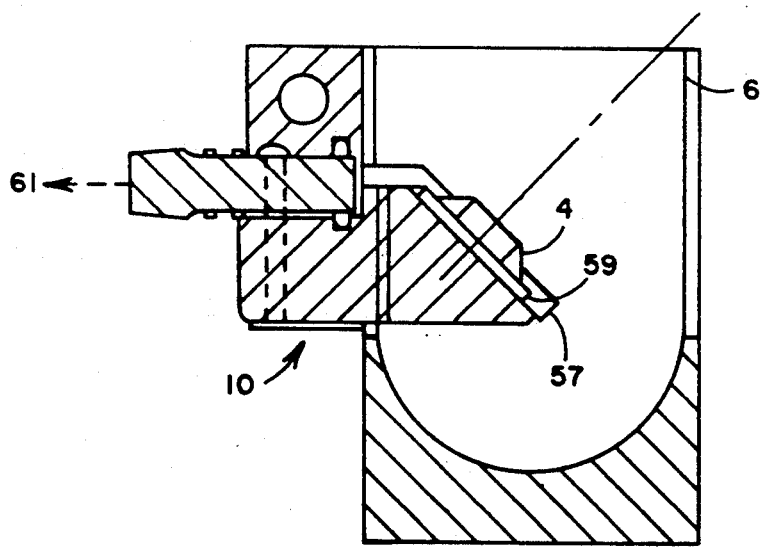

FIG. 5C is a cross-sectional view of the refractometer system. The drain cup (drain port) 6 surrounds the container (sample well) 4 which is attached to the sensor holder 10. There is a cover 57 over the base 59 of the container 4. The sample container 4 is positioned such that there is an angle between the horizontal plane of the liquid in the container, and the omega sensor 2. The range of this angle is about 30° C. to 60° C.; a preferred angle is about 45°. The sensor 2 connects to an optical-electric module 12 (FIG. 1) and with a light source and a detector 61. Lasers may be used as a source in some embodiments. There is a drain hole 55. In an illustrative embodiment, the linkage is via an optional bulkhead connector (AMP Part No. 228045-1) and optimate connectors (AMP Parts No. 530954-4 and 861403-7) which couple the fiber to an LED and photodetector, and then to a component 61 of a larger automated system, e.g., ATLAS, under development to be manufactured by Miles Diagnostic Division, for computation of the specific gravity.

Figure 6:
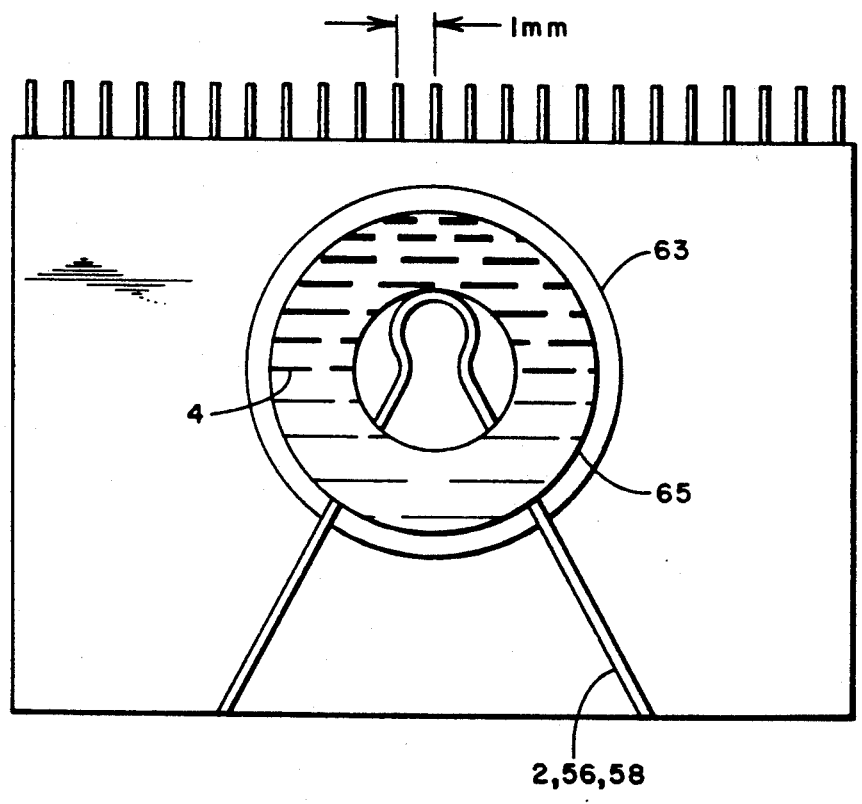
FIG. 6 is a photograph of a plan view of components of an omega-shaped fiber optic specific gravity sensor.

FIG. 6 is an actual planar photograph showing the ESKA fiber 56, 58 winging out from a container embodiment of a volcano-rimmed well 4. The well is set in a base 63 with a Riston ring 65 formed using a photolithographic process involving attachment of a sheet of Dupont Riston TM to a plexiglass and exposing it to an appropriate photomask. In another embodiment, the device is made of molded parts.

4. Sensor Accuracy and Size

Specific gravity accuracy is related to sensitivity, S., and the minimal signal $I_S$ at the detector. Sensitivity to change in specific gravity may be written as $$S = \frac{\Delta \text{signal}}{\Delta SG} \quad (\%/SG \text{ unit}). \tag{2}$$

The absolute sensor signal $I_S$ that is transmitted to the detector when the liquid is plain water can be written as:

$$I_S = CI_0 \epsilon_1 d^2 \ (mw); \text{ where} \tag{3}$$

$I_0$ = input LED intensity (mw)
$\epsilon_1$ = sensor transmission for specific gravity = 1.0 (water)
d = sensor fiber diameter (mm)
C = proportionality constant.

Modeling efforts have shown that the sensor output sensitivity, S, is a function of the following parameters:

$$S = S\left(n_c, \frac{R}{d}, N_b\right). \tag{4}$$

where
$n_c$ = refractive index of the waveguide core,
R/d = bend radius of the sensor (R) ratioed to the fiber diameter (d) as shown in FIG. 2, and
$N_b$ = number of bends.

The above equation indicates that sensor sensitivity is dependent on sensor design. No closed-form solution was found to exist for Equation (4). That means there is no general solution so an empirical solution was obtained. Therefore, a specific sensor design was determined by using a computer-based ray-tracing program.

In general, sensitivity refers to the slope of the line showing the change in the signal for a change in a given parameter, e.g., refractive index. A relatively flat slope requires a very sensitive assay. Accuracy refers to how close an estimate is to the true value. Good sensitivity makes it easier to get good accuracy.

The omega sensor (see FIG. 2) was chosen because it has several bends for increased sensitivity and input-/output fibers are pointed in the same general direction. Four or more bends are also within the scope of this invention, although increases in the number of bends reduces the intensity of the signal so a sensitivity-detection balance must be considered. As explained earlier, this sensor could be easily formed by heating three pins, and bending an ordinary optical fiber around the pins.

The ray-trace model was used to compute the output from an omega sensor. Using this model, the following parameters were selected for equation 4:

$$R/d = 3$$

$$n_c = 1.49$$

$$N_b = 3 \qquad (5)$$

The calculated sensitivity for these input parameters was 40 percent (i.e., 40% change in signal for an SG change of 0.05). This sensitivity was 4 times that considered minimum to attain 0.001 accuracy in SG measurement.

As stated above, sensor overall transmission, $\epsilon_1$, for liquid index $n_l = 1.333$ (i.e., water media) is also important. If the transmission is too low, then not enough signal will reach the detector. Based on ray-trace calculations, the sensor transmission at specific gravity = 1 (i.e., $\epsilon_1$) may be expressed as $\epsilon_1 = f(1/S^N)$ where S is the sensitivity and N is an integer greater than 1. $\epsilon_1$ should be kept ~0.1. For the above set of parameters in Equation (4), $\epsilon_1$, was calculated by the ray-trace model to be approximately 0.08. Therefore, a sensor based on the parameters given in Equation (4) is considered near optimum for the present design conditions. For the present design, d = 0.25 mm was selected (common fiber size). Therefore, R = 0.75 mm ($\approx$ 1/32 inch).

5. Range of Parameters

In general, the parameters for any given sensor are derived from the sample and flush volumes required to reduce carryover sufficiently to provide accurate analyses. For example, when the sample container in a urinalysis has a height of about 2 mm, the amount of water or urine needed to flush out the container and provide a reliable sample for measurement should be at least about 5 to 6 volumes of liquid/volume of the sample container. Therefore, if $\approx$ 250 µl are available for a urine sample well and a water flush, then the sample well volume should be about 50 µl. Given the volume and well height of 2 mm, a well diameter D of about 4.5 mm was calculated.

The sensor fiber diameter is selected so the omega sensor can fit into the bottom of the 4.5 mm diameter well and provide accurate values. If the sample volume limit were to be changed, then the sensors would have to be scaled accordingly.

The height, h, cannot be increased much beyond 2 mm or it becomes difficult to clean out all the sample. However, h can be smaller than 2 mm as long as the fiber sensor is covered with sample. Therefore, $$2 \text{ mm} > h > 2d \qquad (6)$$

It was found that for an h of about 1 mm, bubbles did not readily form in the well during sample or flush water injection. The presence of bubbles on sensor surface can cause a slight error in SG measurement.

The angle 8 may range from about 30° to about 60°. Outside this range it becomes difficult to flush out the well or introduce the sample.

The fiber core refractive index ($n_c$) may be lowered to provide better sensitivity. However, $n_c$ must be greater than the index of high specific gravity urine (about 1.37). Therefore, $n_c$ should be greater than 1.37, but not so great as to detract from accuracy and sensitivity. A preferred range of values for $n_c$, accordingly, is between about 1.4 and 1.5.

Presently, plastic fiber made of PMMA ($n_c = 1.49$) is preferred in the practice of the invention. Fibers with lower $n_c$ would be more desirable, as they become available.

All the other parameters ($N_b = 3$, R, d) are fixed, once the urine sample volume (i.e., well diameter and height) is selected. They may be bigger or smaller depending on the sample volume restriction. However, $R/d \geq 3$ should be used so that sensor transmission is high ($\epsilon_1 \geq 5\%$), yet sensitivity is good ($S \geq 30\%$). These S and $\epsilon_1$ values are required for maintaining good measurement accuracy.

Any characteristic linked to refractive index may be computed by use of this device. It is not limited to specific gravity determination.

EXAMPLES

The following examples disclose the specific performance of the omega sensor embodiment used in the device for measuring specific gravity.

The specific gravity measurement range of the omega-shaped sensor was 1.00 to at least 1.09. This range includes values expected for urines to be measured for clinical and veterinary purposes.

EXAMPLE 1

Sensitivity

Figure 7:
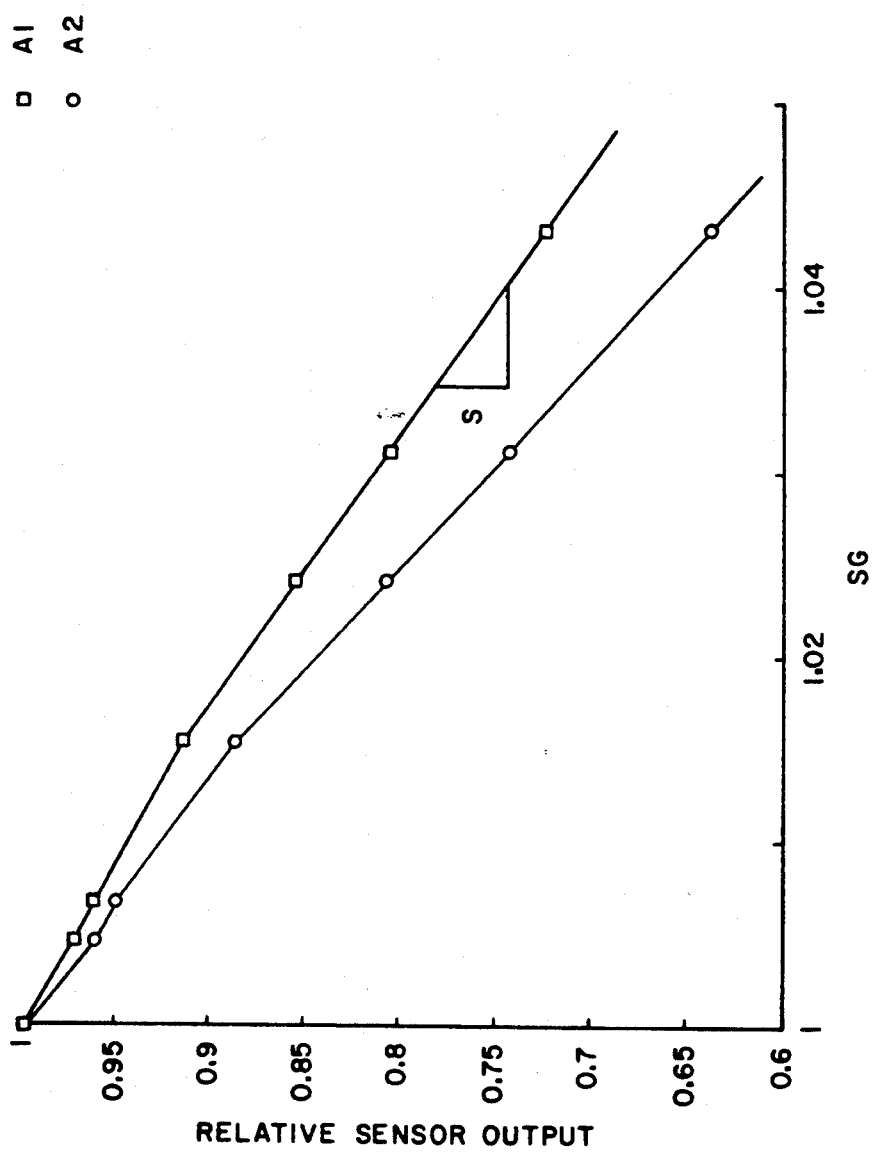
FIG. 7 is a graph indicating sensor specificity wherein the X-axis shows specific gravity and the Y-axis shows relative sensor output.

To test the sensitivity, range and accuracy of the sensor, solutions of known specific gravity were put into the specific gravity measurement container and the output light intensity was recorded relative to a specific gravity of 1.0. An example of this specific gravity calibration on preliminary versions of the sensor is shown in FIG. 7. A1 and A2 refer to the two sensors tested to give these results. A change in the slope of the lines occurs at about 1.02 specific gravity units. The slope of the lines indicate sensitivity.

Table 1 presents results on six later versions of sensors. In this Table, $S_{1.05}$ refers to the percent change in relative sensor output for a 0.05 change in specific gravity, i.e., from 1.00 to 1.05.

TABLE 1

| SENSOR CHARACTERISTICS | | | |
|---|---|---|---|
| Sensor # | $\epsilon_1$ | $S_{(Slope)}$ | $S_{1.05(\%)}$ |
| A0 | .16 | 7.14 | 36 |
| A1 | .14 | 6.00 | 30 |
| A2 | .11 | 8.90 | 45 |
| B1 | .08 | 8.83 | 44 |
| B2 | .11 | 7.50 | 38 |
| B3 | .10 | 6.92 | 35 |

Average Results $S_{1.05} = S \times (0.05) \times 100$
$\epsilon_1 = 0.12 \pm 0.03$
$S = 7.55 \pm 1.13$
$S_{1.05} = 38 \pm 5.7\%$

EXAMPLE 2

Temperature Error

At times, there can be differences between sample temperature and the wash solution (i.e., room) temperature. Under these circumstances, specific gravity errors can result. There are two sources of measurement error due to temperature:

1. Density change of liquid due to temperature change (not a sensor error).

2. Sensor induced temperature error (assuming density held constant).

The first source is due to the physical fact that a liquid's density will change with temperature. Therefore, an error will result when the sample density measurements are not referenced to room temperature conditions. If the flush water is at the same temperature as the urine samples (i.e., room temperature variations only), the error should be minimal due to density changes. However, if the urine is at a different temperature than the flush water, a small measurement error will result.

A second source of error could come from the sensor itself. For example, some temperature change of the fiber material could change the waveguide index and, hence, the sensor output.

An experiment was designed to test both sources of error simultaneously. Water (specific gravity=1.00) and a 1.043 specific gravity solution were heated and cooled over the range from 6° to 48° C. and sensor specific gravity values were obtained using a standard calibration curve (i.e., room temperature calibration). The results of these measurements are shown plotted in FIG. 8.

Note in this figure that the indicated specific gravity value decreases with increasing temperature (as expected) due to the reduced density effect. The slope of this measured specific gravity versus temperature change was found to be $-1.5 \times 10^{-4}$ (° C.)$^{-1}$ for water and $-1.1 \times 10^{-4}$ (° C.)$^{-1}$ for specific gravity = 1.043 solutions. Therefore, a ±7° C. change (from the flush solution temperature) for a water sample and a ±9° C. change for specific gravity=1.043 sample will result in a ±0.001 specific gravity error. Saying this another way, for a 10° C. to 35° C. temperature difference the water sample measurement will indicate a specific gravity of 0.9978 to 1.0015. This is an error of 0.0023 at 10° C. and 0.0115 at 35° C. Only over the range from 18° C. to 32° C. will the error for a water sample be within the ±0.001 specific gravity error range. Therefore, the sample temperature must be kept within this temperature difference from the wash solution or errors greater than ±0.001 will result for a water sample.

The lower error for higher specific gravity solutions is probably due to thermal conductivity effects. Because the specific gravity=1.043 solution slope is lower in FIG. 8, the temperature range for ±0.001 can be larger (i.e., 15° to 35° C.). Therefore, only for the 10° to 15° C. range will the error exceed the specified level. At 10° C., the reading for a specific gravity=1.043 solution would be 1.0414 (error=−0.0017).

Figure 8:
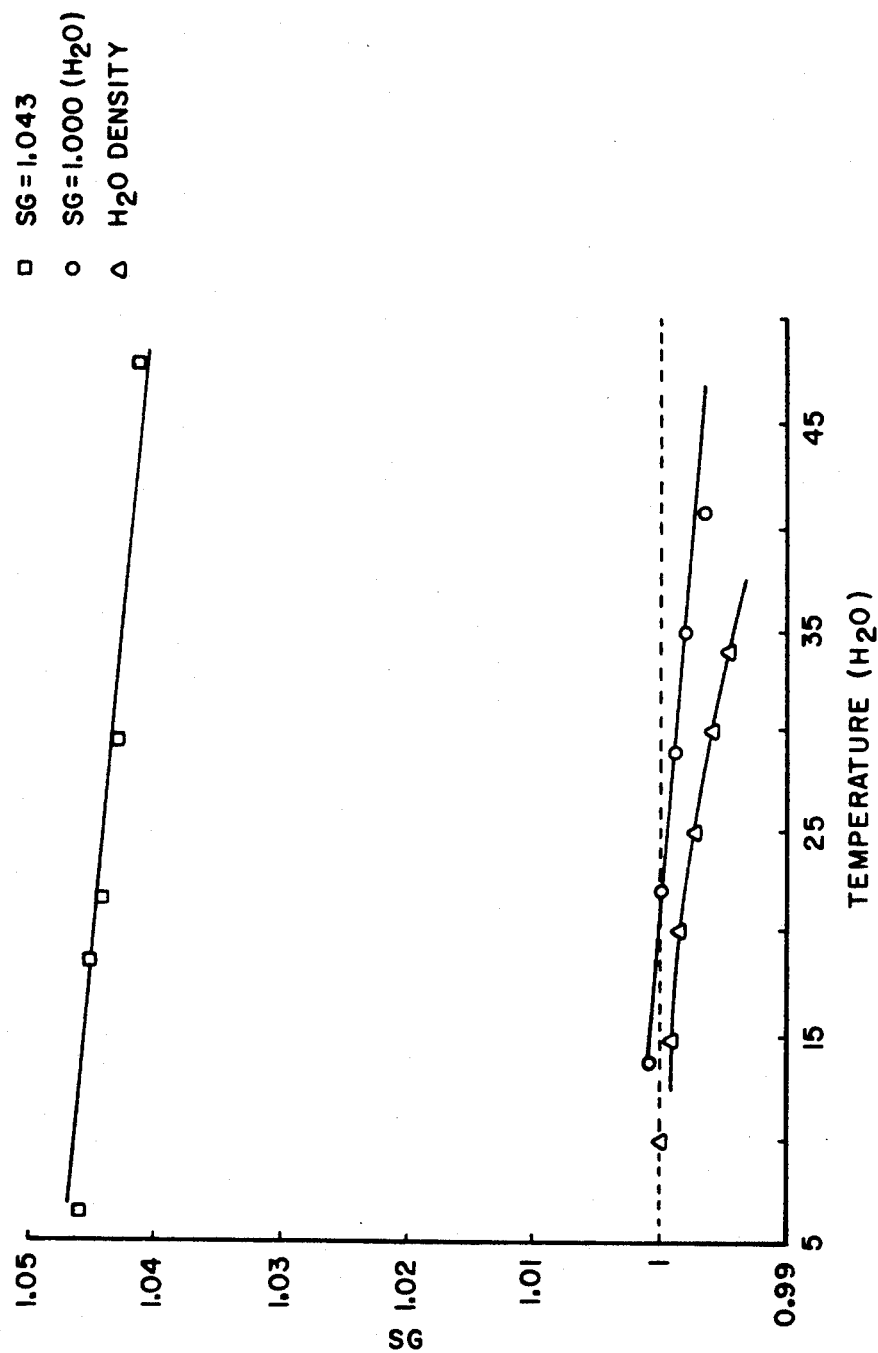
FIG. 8 is a graph of temperature vs. specific gravity showing the density change of a liquid as temperature changes, and sensor-induced temperature error.

Also shown in FIG. 8 is the plot of water density as a function of temperature. For the 10° to 25° C. range, the slope variation of this curve is almost the same as the slope variation of the measured specific gravity versus temperature curve of the omega sensor. This indicates that the sensor measurement error is solely due to sample density changes and has nothing to do with the sensor itself. In fact, the sensor actually tends to compensate for error due to temperatures above 25° C. because less error results than is expected from a sample density change only. The fiber core index change with temperature is most likely accounting for this sensor temperature compensation effect.

In summary, room temperature variations should produce negligible errors because sample and wash solutions are at the same temperature. But, temperature differences between sample and wash solution can cause errors due to sample density effects. The omega sensor itself, tends to reduce temperature errors due to sample temperature changes. However, slightly greater than ±0.001 specific gravity errors will result if the sample-to-flush water temperature differences are not kept to within a ±7° C. range.

EXAMPLE 3

Turbidity Effects

Test sample solutions were first prepared using clear water and higher specific gravity solutions with known amounts of 3 μm silica particles added. These samples were milky white in appearance and the particle loading ranged from 0.07 to 10 grams per liter (g/l). These turbid test samples were allowed to set until the particles settled then the specific gravity turbidity test was performed as follows:
1. Specific gravity of the clear supernatant was first measured using the omega sensor.
2. Sample was then agitated to suspend the particles and the specific gravity value was determined on the turbid sample using the omega sensor.

It was noted that turbid sample output signal from the specific gravity sensor first slightly exceeded sensor output for the clear liquid, but then the signal dropped exponentially with time as particles settled in the well. Readings were obtained at two seconds following initiation of sample injection and these sensor readings were used to calculate any turbidity induced error. The two-second time interval was chosen to reflect the expected time available to make the actual urine specific gravity measurement in an automated system for multi-test urinalysis.

Figure 9:
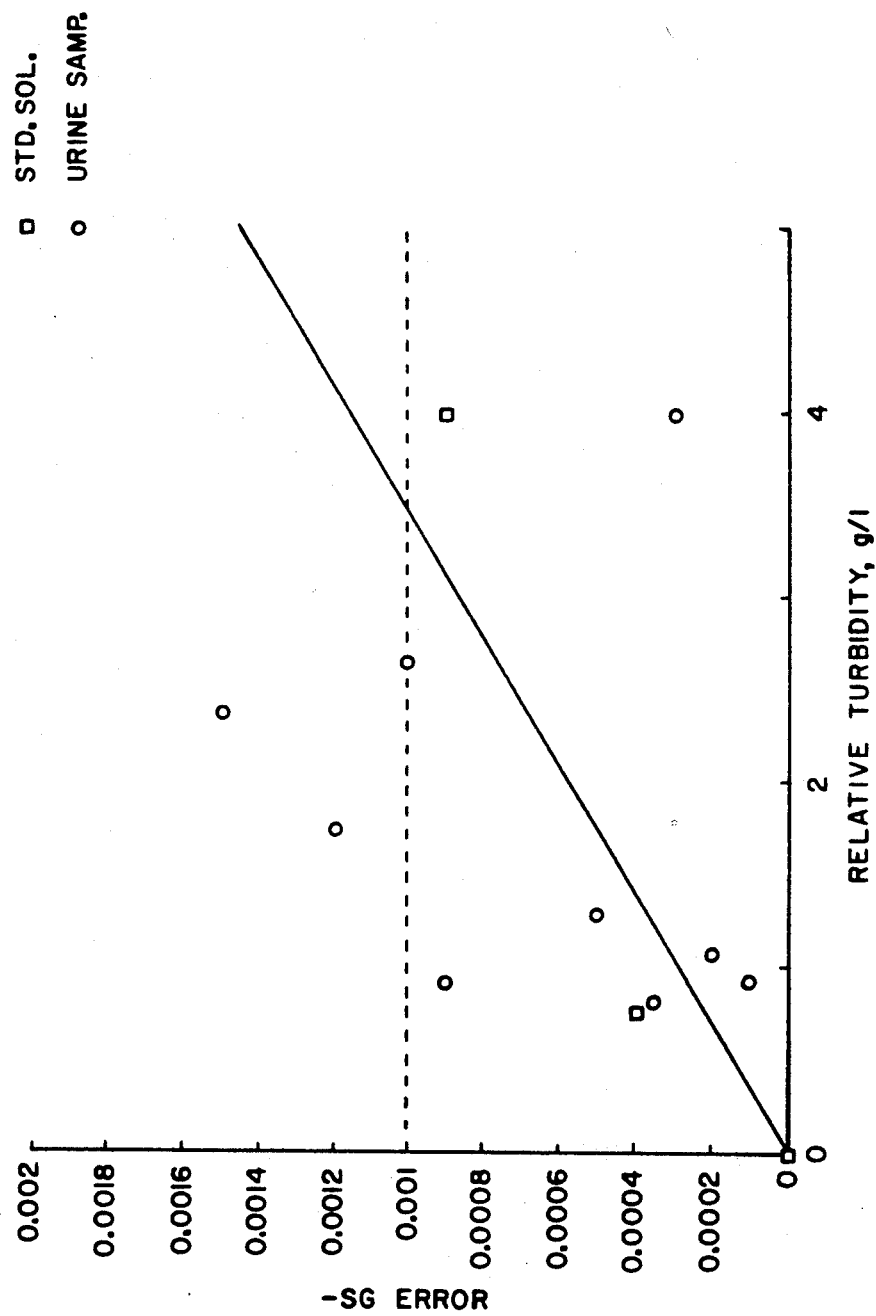
FIG. 9 is a graph of turbidity of various urine samples versus error in specific gravity measurements.

Results of the specific gravity tests are shown in FIG. 9 for the standard test solutions (solid symbols) discussed above and for nine turbid urine samples collected at Riverside Methodist Hospital (Columbus, Ohio). The actual turbid urine samples were considered to be the nine of the most turbid urines of all samples collected over a 3-day period (approximately 300 samples). Note in FIG. 9 that the error is always negative (lower specific gravity value than for clear solution) and that the error generally increased for increasing particulate loading.

It can be seen that for particulate loading less than approximately 4 g/1, the specific gravity measurement error is within the ±0.001 range. However, two of the nine urine samples resulted in a slightly larger error (i.e., ±0.0015 error). Therefore, approximately 2/300 (0.7 percent) of the time, a specific gravity error of up to 0.0005 units greater than allowable can occur due to turbidity effects. These data show that, in general, the omega sensor is only minimally affected by the presence of turbidity in a urine sample.

EXAMPLE 4

Carryover Effects of Flushing

The effectiveness of flushing out the container will vary with:
1. Volume of water flush solution;
2. Specific gravity level of sample volume to be flushed.
3. Sensor system design (mainly the container and holder design), and
4. Position of the pipette in the container during flushing.

Data was obtained for specific gravity error as a function of liquid specific gravity for two different water flush volumes (200, 300 μl). These data are plotted in FIG. 10. As the specific gravity level of the solution increases, the positive measurement error, after water flush, also increases. This is due to the fact that a small amount of specific gravity solution remains in the container and the mixing of this solution (specific gravity > 1.0) with the water (specific gravity = 1.0) raises the actual well specific gravity level slightly. It can also be determined from FIG. 10 that a water flush volume of approximately 300 µl is required to keep the specific gravity error within ±0.001. If only 200 µl of water flush is used, the error in specific gravity may exceed this level for sample specific gravity above 1.02.

Figure 10:
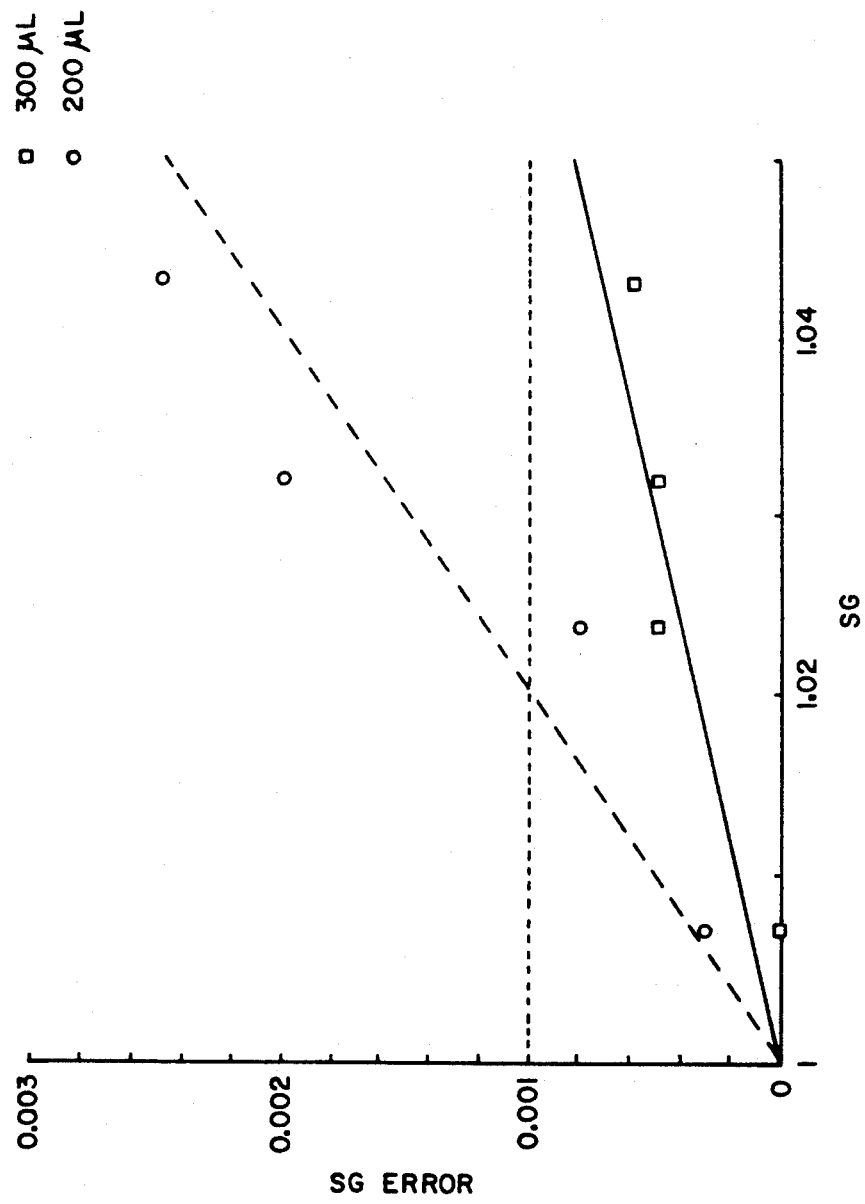
FIG. 10 is a graph of specific gravity (X-axis) versus sensor error due to well carryover (Y-axis) for 200 and 300 μl flush volumes.
Figure 11:
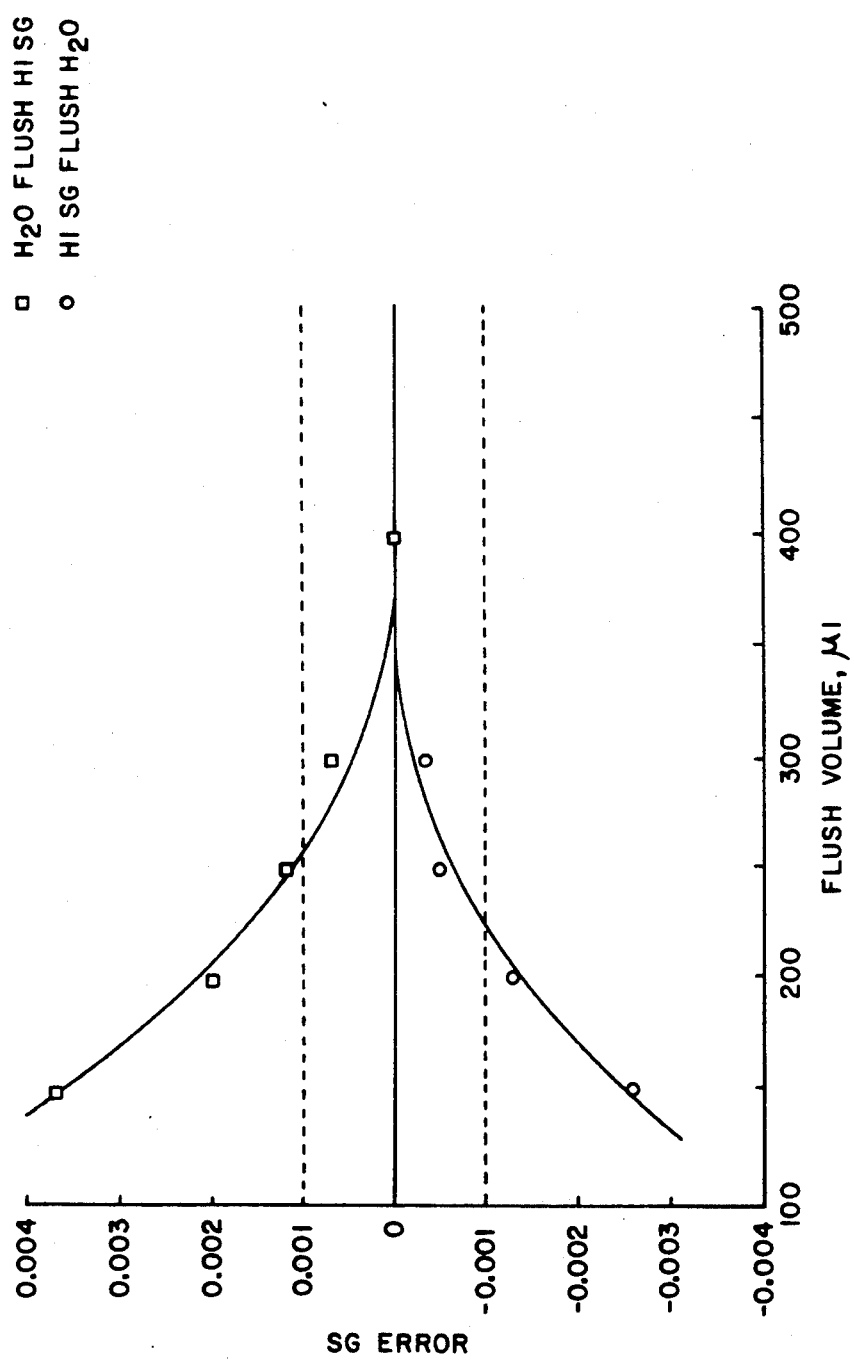
FIG. 11 is a graph of the effects of flush volume on the sensor well carryover error and results of a water flush and a high specific gravity liquid (~1.043)

Based on the data in FIG. 10, one of the worst case (human) specific gravity solution (specific gravity = 1.043) was used, in further experiments, to better define specific gravity sample and water flush volumes. These data are shown in FIG. 11. In this experiment, the well was filled first with specific gravity = 1.043 solution and increasing amounts of water were used to flush out (via pipette) the well. Data in FIG. 11 indicate that at least 250 µl of water would be required to maintain the ±0.001 error requirement.

Further tests were performed where water was placed in the well and specific gravity = 1.043 solution was pipetted into the well to clean the water solution prior to a specific gravity test. In this case, approximately 225 µl of sample of a specific gravity = 1.043 (simulated urine) is required to keep the measurement error below the ±0.001 level.

EXAMPLE 5

Pipette Carry Over Error

Figure 12:
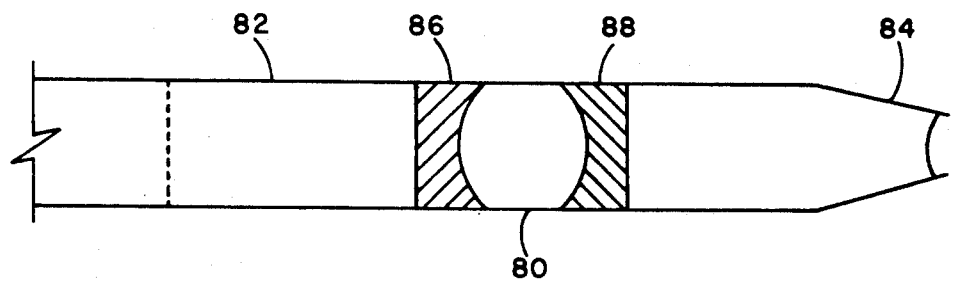
FIG. 12 is a diagram of the component locations of a pipette showing an air pig to minimize carryover error.

Another source of error in the specific gravity measurement is pipette carryover which occurs because a small amount of water mixes with the urine sample at the water/urine interface during sample pipetting. The reverse is also true, resulting in some urine mixing with the flush solution. This will result in pipette induced carryover errors because the sample and flush (which is used for calibration) becomes contaminated. A method for minimizing this problem is shown in FIG. 12.

As shown in this figure, an air bubble 80 (or air pig as it has been called) is used to separate the water flush 82 and urine sample 84 fluids. The existence of this air pig minimizes mixing of the two solutions, hence, minimizes pipette contamination errors. To further minimize the error, a small amount of liquid on either side of the air pig can be considered as "waste solution" 86, 88. Therefore, some amount of sample (50 µl in FIG. 12) is left in the pipette (not pipetted into measurement well). Presumably, this waste sample contains the majority of water contamination so leaving it behind improves the sample specific gravity measurement error.

Further, an additional amount of water (50 µl in FIG. 12) is used so that the total flush volume is 300 µl (250 required + 50 waste) to provide improved water calibration error results.

EXAMPLE 6

Response Time

Sensor response time is less than about 0.2 seconds. The water flush takes about 1 second. Electronic readout time is about 1 second down to about $50 \times 10^{-6}$ sec. The total time for a specific gravity readout on a liquid sample is therefore about 2.2 seconds.

EXAMPLE 7

Effects of Protein Buildup

Possible protein buildup on the sensor was assessed by measuring any long-term changes in the sensor calibration with continuous exposure to a protein solution. The protein test sample was prepared using Checkstix ™ solution (specific gravity = 1.007), which was laced with 1030 mg/dl of bovine serum albumin.

The experiment was conducted as follows:
1. After fabrication, the sensor was calibrated using various specific gravity solutions.
2. This sensor was then inserted into the protein laced solution for a fixed exposure period.
3. Measurements were repeated using various known specific gravity solutions to determine measurement error (original calibration data used to calculate specific gravity after exposure).
4. Exposure and measurement continued for additional time periods up to a total of 110 hours.

Figure 13:
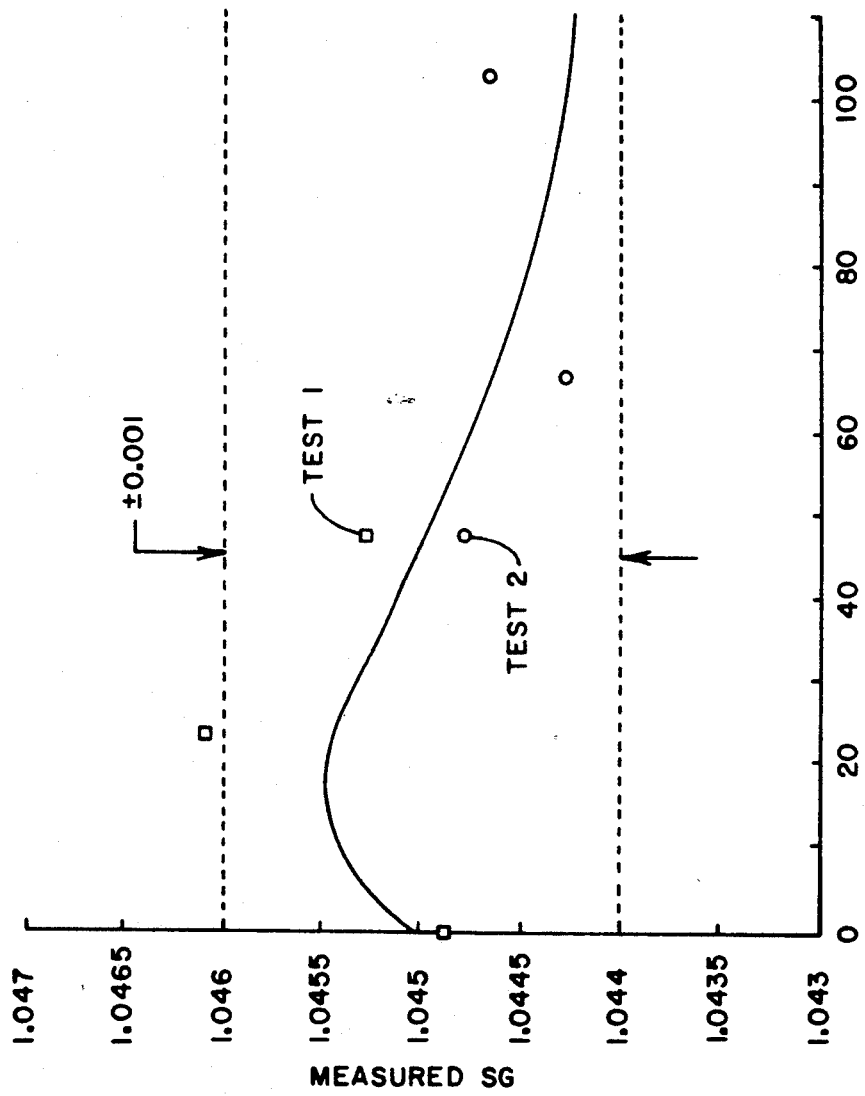
FIG. 13 is a graph which presents results of protein exposure tests for a sensor designated A2 wherein exposure time is plotted against specific gravity for two experiments (tests).

The error data for two exposure tests are shown in FIG. 13. Note that the measured specific gravity value first increased to a maximum error of +0.001 within 24 hours of exposure, then dropped in an exponential fashion to an error value near −0.001 after 100 hours of exposure to the protein solution. These data indicate that the sensor error is about ±0.001 for over 100 hours at high levels of protein exposure.

The data in FIG. 13 can be used to estimate the long term performance of the specific gravity sensor. These data indicate that for 110 hours, the slope of the relative output version specific gravity plot (see FIG. 7) changed by only a small amount (decreased ≈3 percent). Therefore, an extrapolation of the 110 hours to clinical conditions could indicate the total sensor life. Using the same argument provided above, regarding 20% urine versus 80% water exposure of the sensor, the 3 percent change may occur at 550 hours after exposure to only high protein urine. Fortunately, protein levels exceed 30 mg/dl only 1 out of every 4 urine samples from hospitals, (Miles) so the actual sensor life time would likely be at least 2200 hours.

After exposure to protein solutions, the sensor was easily returned to its zero exposure condition by placing it in distilled water for an equal time period. Therefore, the alternate exposure of the sensor to urine then to water may prevent any protein layer from building up no matter how long the exposure time.

I claim:

1. A device for measuring the specific gravity of a small amount of liquid comprising:
   (a) a dispenser for the liquid;
   (b) a container positioned under the dispenser to receive the dispensed liquid;
   (c) a sensor having multiple reverse bends mounted within the container for immersion in the liquid, said sensor measuring the refractive index of the liquid; and
   (d) a module connected to said sensor to calculate the specific gravity of the liquid based on the refractive index of the liquid and that of water, both of which are measured in said container.

2. The device for measuring the specific gravity of a small amount of a liquid of claim 1 wherein the dispenser comprises a pipette.

3. The device for measuring the specific gravity of a small amount of a liquid of claim 1 wherein the container comprises a well.

4. The device for measuring the specific gravity of a small amount of a liquid of claim 3 wherein the well comprises a volume of about 30-$\mu$l.

5. The device for measuring the specific gravity of a small amount of a liquid of claim 3 wherein the well comprises a diameter of about 4.5 mm and a height not greater than about 2 mm.

6. The device for measuring the specific gravity of a small amount of a liquid of claim 1 wherein the sensor is positioned at about a 30°-60° angle to a horizontal plane of the container.

7. The device for measuring the specific gravity of a small amount of a liquid of claim 1 wherein the liquid comprises a biological sample.

8. The device for measuring the specific gravity of a small amount of a liquid of claim 7 wherein the biological sample comprises urine.

9. The device for measuring the specific gravity of a small amount of a liquid of claim 1 wherein the specific gravity of the liquid calculated is from about 1.00 to 2.00 units, wherein the refractive index of water is 1 unit.

10. The device for measuring specific gravity of a small amount of liquid of claim 1 wherein said sensor has a radius of curvature in the reverse bends amounting to about 2 to about 4 times the cross-sectional diameter of the sensor.

11. The device for measuring the specific gravity of a small amount of liquid of claim 10 wherein said sensor is omega shaped.

12. The device for measuring the specific gravity of a small amount of liquid of claim 1 wherein said container has a diameter of about 3 to 5 millimeters and a height of about 1 to 3 millimeters.

13. A method for measuring the specific gravity of a liquid comprising:

(a) placing a first volume of water in a container;
(b) flushing the first volume of water out of the container by introducing a first volume of a liquid whose specific gravity is to be measured into the container;
(c) recording the refractive index signal of the first volume of the liquid by means of a sensor;
(d) flushing the first volume of the liquid out of the container by introducing a second volume of water into the container;
(e) recording the refractive index signal of the second volume of water by means of a sensor; and
(f) computing the specific gravity of the liquid using the refractive indices signals of the first volume of liquid and the second volume of water.

14. The method for measuring the specific gravity of a liquid of claim 13 wherein said steps of recording the refractive index signal of said first volume of the liquid and recording the refractive index of the second volume of water include the steps of passing light through a fiber optic member comprising said sensor and on to be measured by a photodetector.

15. The method for measuring the specific gravity of a liquid of claim 14 wherein there is a loss of transmitted light from the sensor into the liquid, said loss being a function of the refractive index of the liquid.

16. The method for measuring the specific gravity of a liquid of claim 14 wherein the specific gravity of the liquid is calculated in reference to the specific gravity of the water by setting the specific gravity of water to be 1.

17. The method for measuring the specific gravity of a liquid of claim 14 wherein between about 300 and 500 microliters of water are employed as the second volume of water.

18. The method for measuring the specific gravity of a liquid of claim 14 wherein the temperature is maintained between about 10° and about 35° C. while specific gravity measurements are being made.

* * * * *